United States Patent
Fichera et al.

(10) Patent No.: US 6,936,224 B2
(45) Date of Patent: Aug. 30, 2005

(54) APPARATUS AND PROCESS FOR TRANSPORTING SAMPLE PLATES

(75) Inventors: Stephen L. Fichera, Lawrence, MA (US); Richard L. Victor, Jr., Mendon, MA (US)

(73) Assignees: PerSeptive Biosystems, Inc., Framingham, MA (US); MDS Inc. through its MDS Sciex Division, Concord (CA)

( * ) Notice: Subject to any disclaimer, the term of this patent is extended or adjusted under 35 U.S.C. 154(b) by 556 days.

(21) Appl. No.: 09/886,734

(22) Filed: Jun. 21, 2001

(65) Prior Publication Data

US 2002/0197722 A1 Dec. 26, 2002

(51) Int. Cl.$^7$ ................................................. B32B 5/02
(52) U.S. Cl. ............................ 422/63; 422/66; 436/43; 436/46; 436/47; 436/48
(58) Field of Search .............................. 436/43, 46, 47, 436/48, 807, 808, 44; 422/63, 66

(56) References Cited

U.S. PATENT DOCUMENTS

| | | | |
|---|---|---|---|
| 4,219,529 A | * | 8/1980 | Tersteeg et al. ............... 422/65 |
| 4,424,191 A | | 1/1984 | Jakubowicz |
| 4,584,275 A | | 4/1986 | Okano et al. |
| 4,807,984 A | | 2/1989 | Kurimura et al. |
| 5,736,102 A | * | 4/1998 | Seaton et al. .................. 422/65 |
| 5,952,831 A | * | 9/1999 | Yamakoshi et al. .......... 324/321 |
| 6,111,251 A | * | 8/2000 | Hillenkamp ................. 250/288 |
| 6,133,045 A | * | 10/2000 | Johnson et al. .............. 436/177 |

FOREIGN PATENT DOCUMENTS

WO    WO 96/03768    2/1996

* cited by examiner

Primary Examiner—Jill Warden
Assistant Examiner—LaToya Cross
(74) Attorney, Agent, or Firm—Andrew T. Karnakis

(57) ABSTRACT

A process and apparatus are provided for simultaneously moving a first sample plate into an analytical apparatus and a second sample plate from the analytical apparatus. The first sample plate is moved on an entry path which is vertically spaced apart from an exit path for the second sample plate. The transfer mechanism is disclosed in operation with a MALDI-TOF mass spectrometer.

20 Claims, 11 Drawing Sheets

FIG. I

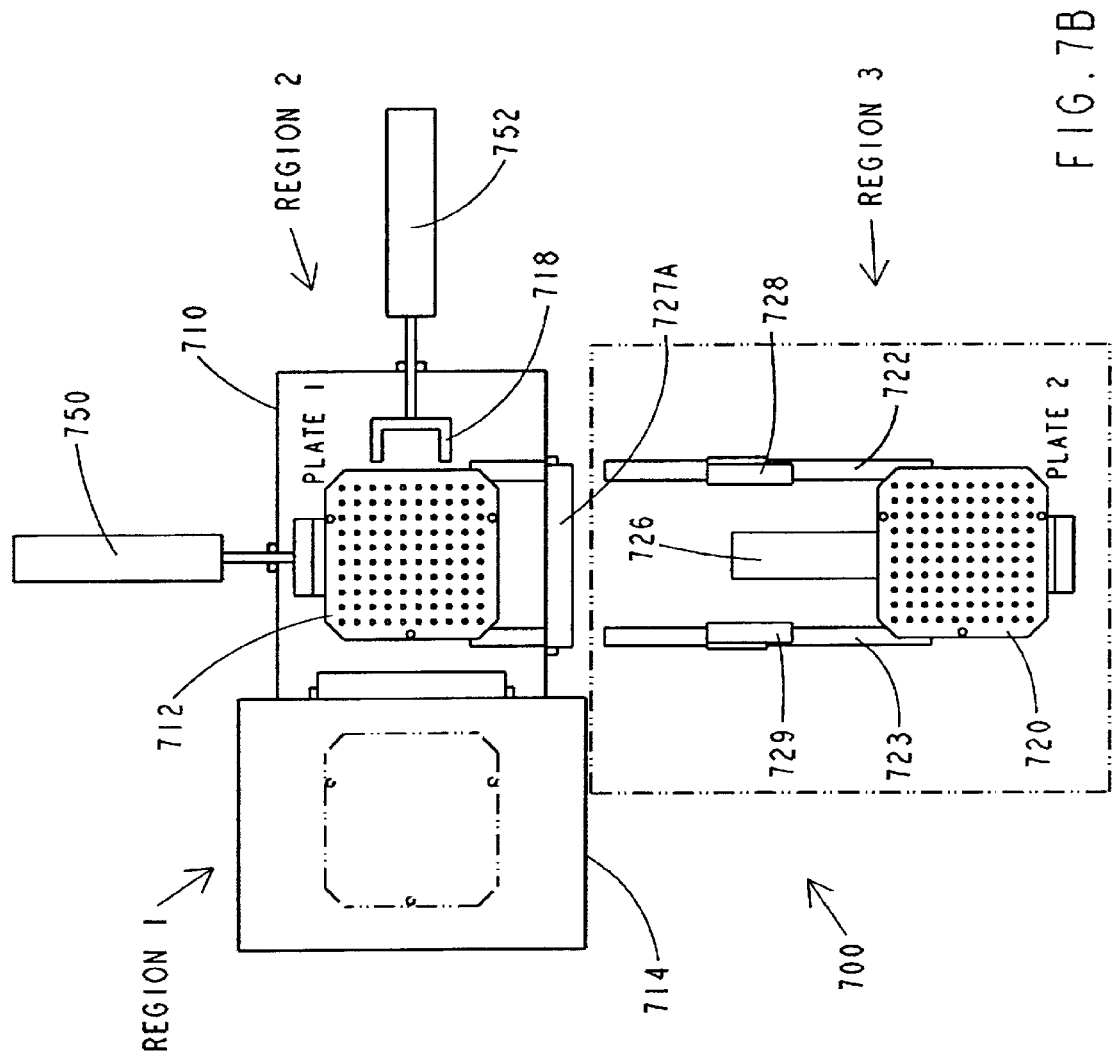

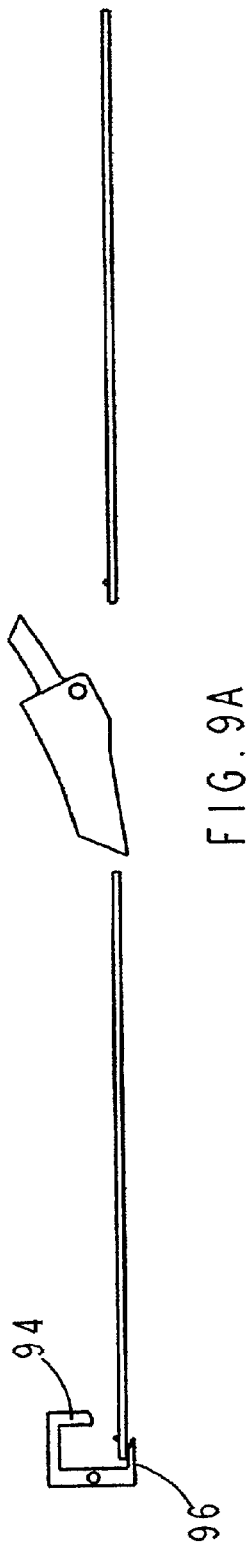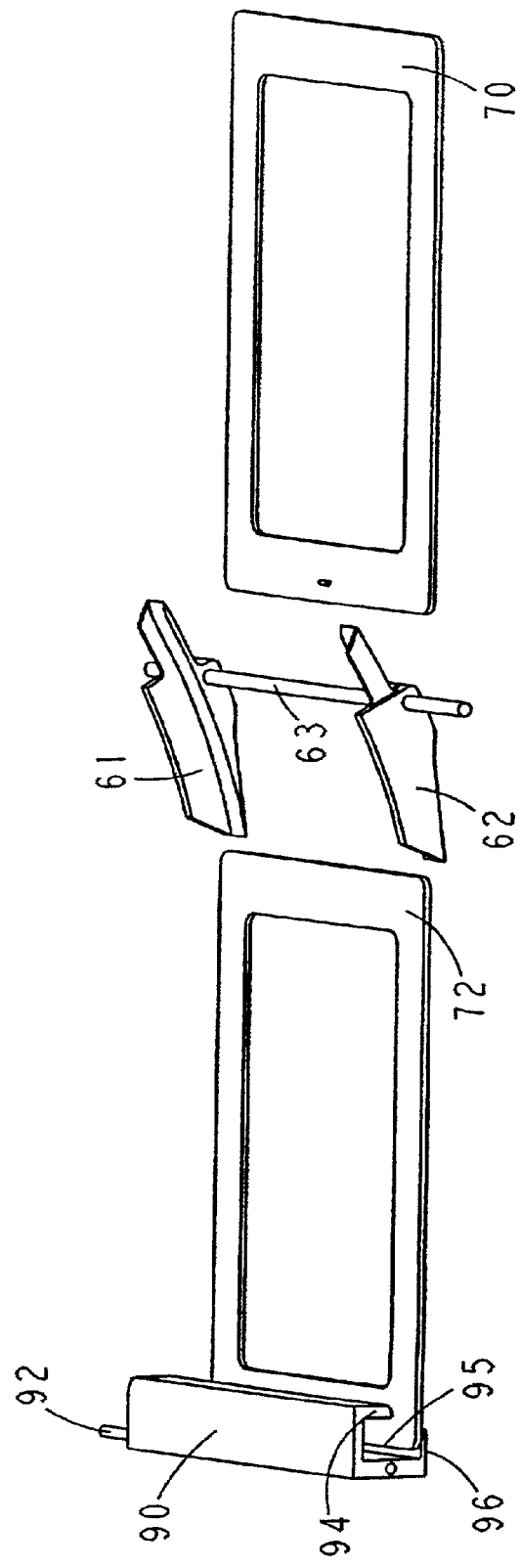

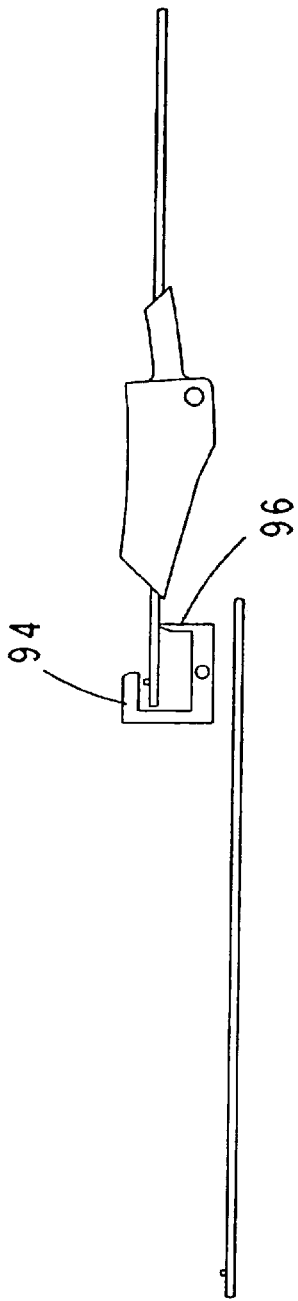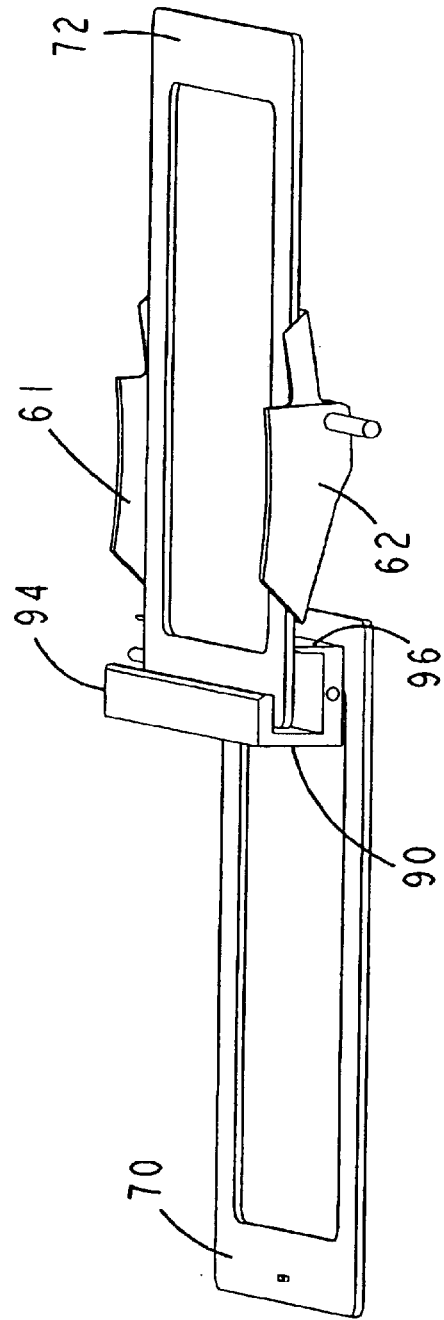

APPARATUS AND PROCESS FOR TRANSPORTING SAMPLE PLATES

BACKGROUND OF THE INVENTION

This invention relates to an apparatus and process for transporting sample plates to and from a transfer position to enable the analysis of samples on a sample plate. More particularly, this invention provides such an apparatus and method for simultaneously transporting one sample plate from a point of sample analysis and another sample plate to the point of sample analysis.

Prior to the present invention, a sample plate, usually containing a plurality of liquid or dried samples, has been transported into an analytical apparatus to a point of analysis of samples on the plate by positioning the plate on a support, followed by moving the plate to the point of analysis. After the sample analysis is completed, the sample plate is removed from the analytical apparatus to expose the sample plate which then is lifted from the support. A new sample plate is then positioned on the support and the transport cycle is repeated. Thus, the position for removing the analyzed sample plate from the analytical apparatus is the same position as the start position of the sample plate.

This mode of transporting sample plates is undesirable in certain applications since the analytical apparatus is not utilized during the time required to replace the sample plate in the apparatus with a new sample plate. This, in turn, results in a lowering of the potential analytical capacity of the analytical apparatus. Since presently available analytical apparatus are expensive, and since many applications require rapid or high throughput analysis, this results in increased cost for analyzing samples on a per sample basis.

Accordingly, it would be desirable to provide an apparatus and process for delivering sample plates to an analytical apparatus wherein the time required to deliver sample plates seriatim to a point of sample analysis is minimized. Such a process and apparatus would speed the analysis and thus reduce the cost of analyzing samples on the sample plates.

SUMMARY OF THE INVENTION

In accordance with this invention, an apparatus and process for transporting sample plates to an analytical apparatus is provided wherein one sample plate is delivered on a plate support on an entry path to an analytical apparatus and another sample plate is removed from the analytical apparatus simultaneously. When an analysis of samples on a first sample plate positioned in an analytical apparatus is complete, the first sample plate is moved out of the analytical apparatus on an exit path that is vertically spaced apart from its entry path into the analytical apparatus. That is, the exit path can be positioned above or below the entry path. Simultaneously with movement of the first sample plate away from the analytical apparatus, a second sample plate is moved into the analytical apparatus on the entry path positioned above or below the exit path of the first sample plate. Representative suitable analytical apparatus include a laser induced fluorescence detector, a capillary electrophoresis apparatus, a fluorescent detector, a chemiluminescence detector, a matrix assisted laser desorption ionization (MALDI) mass spectrometer or the like. It is understood that any reference herein to the simultaneous movement of the sample plates into or away from the analytical apparatus is intended to encompass within the scope of the present invention movement to and from an intermediate transfer position associated with the analytical apparatus as well as to and from the direct point of measurement.

The sample plates are moved in a manner that prevents spillage of samples from the sample plates. The first sample plate is removed from the plate support and is replaced by a third sample plate on the support. This transport cycle of sample plates then is repeated.

With the apparatus of this invention, a sample plate is transported to an analytical apparatus by a movable sample plate guide member pushing or pulling the sample plate, as through the use of belts and rollers or gears, or pneumatically on an entry path into the analytical apparatus. A second sample plate positioned within the analytical apparatus is moved in similar fashion away from the apparatus on an exit path vertically spaced apart from the entry path simultaneously with the movement of the first sample plate. The movement path of both transport mechanisms for the first sample plate and the second sample plate are reversed so that both transport mechanisms are repositioned to move subsequent sample plates in the same manner as the movement of the first and second sample plates.

A suitable stop is provided to assure that the sample plates are properly positioned within, or for entry into, the analytical apparatus. A sensor is also provided to sense the position of the sample plate guide members so that reversal of the transport mechanism for moving the sample plates can be properly initiated and stopped, thereby permitting subsequent sample plate movement to be properly initiated and ended.

BRIEF DESCRIPTION OF THE DRAWINGS

FIG. 7B is a schematic representation, in top view, of the apparatus of FIG. 7A illustrating the various positions of MALDI sample plates during a cycle of sample plate exchange in accordance with the present invention.

FIGS. 9A and 9B illustrate an alternative apparatus of this invention at a start position for an arm for moving a sample plate.

FIGS. 10A and 10B illustrate movement of the arm and sample plate of FIGS. 9A and 9B.

DESCRIPTION OF SPECIFIC EMBODIMENTS

The invention is specifically described below with reference to an apparatus which effects movement of two sample plates in vertically spaced apart paths wherein the sample plate exit path is positioned above the sample plate entry path. However, it is to be understood that the sample plate exit path also can be positioned below the sample plate entry path from and into analytical apparatus. All that is needed to position the plate exit path either above or below the entry path are sample plate guide rails and pivotally mounted slides that can be positioned to provide the desired entry or exit path.

Figure 1:
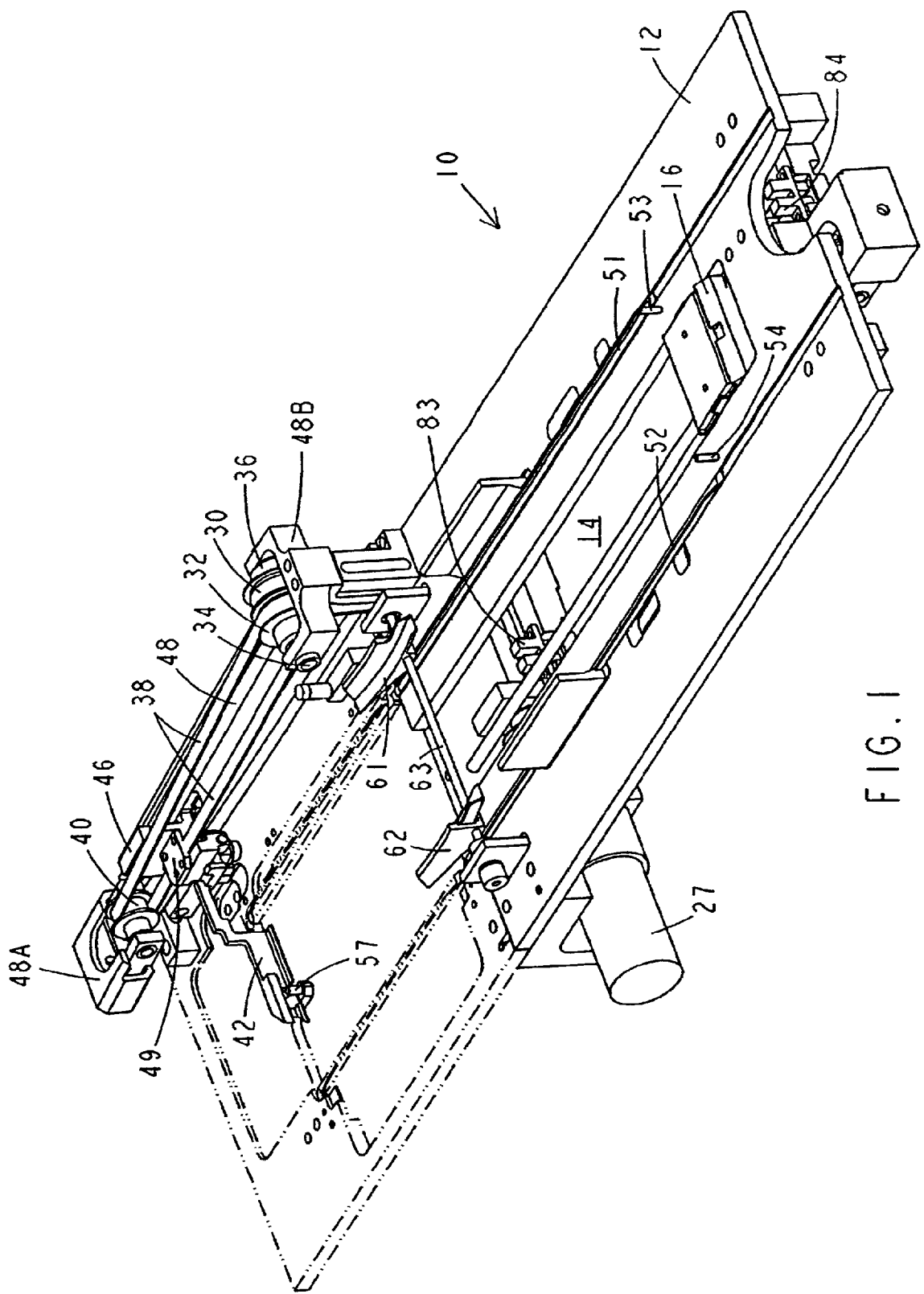
FIG. 1 is a top perspective view of the apparatus of this invention.
Figure 2:
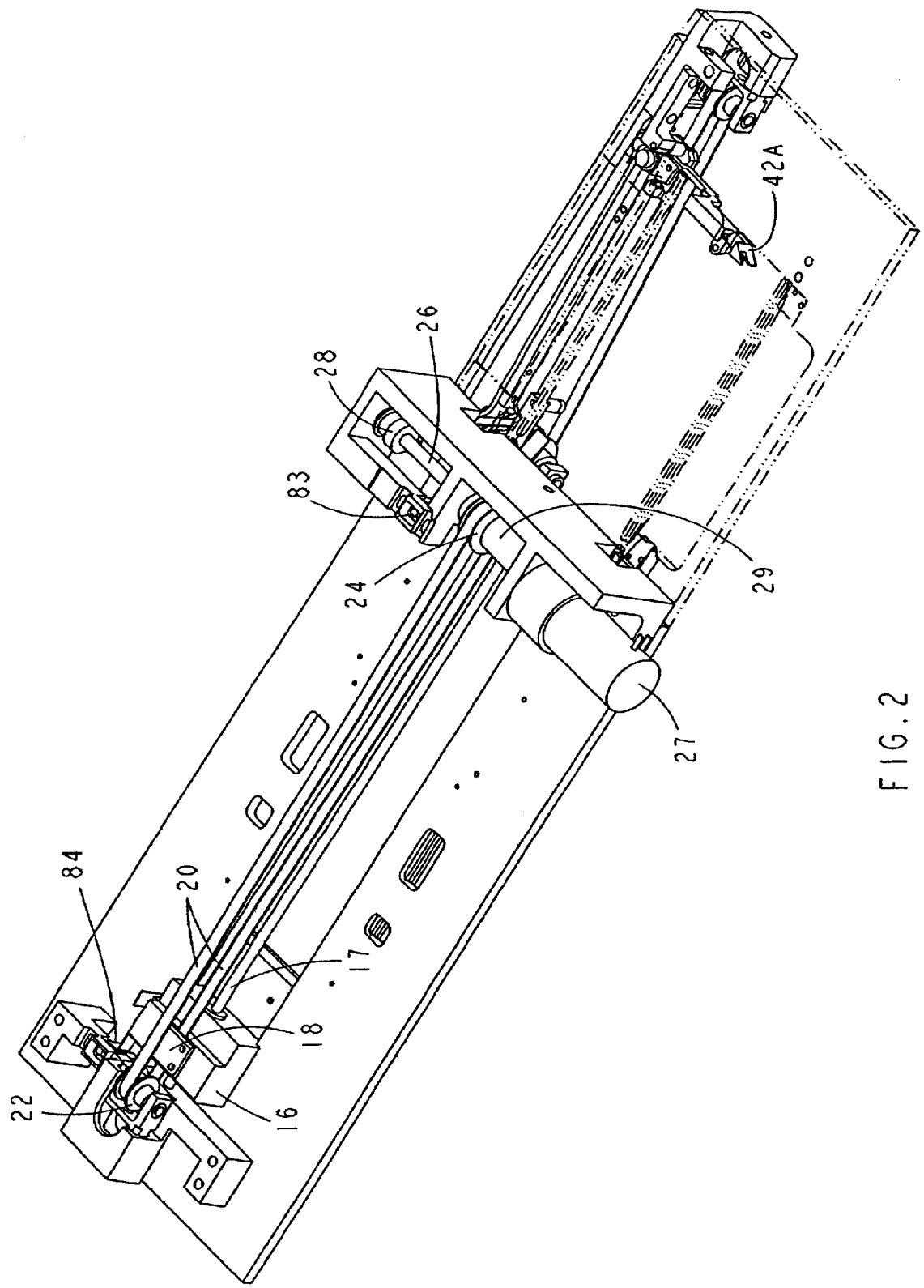
FIG. 2 is a bottom perspective view of the apparatus of FIG. 1.

Referring to FIGS. 1 and 2, the transfer apparatus 10 of this invention includes a support plate 12 having a slot 14. A loader arm 16 is positioned within the slot 14. The arm 16 is mounted on a shaft 17 and is attached to a belt plate 18 which, in turn, captures belt 20. Belt 20 is wound around idler roll 22 such as a spring loaded idler roll and drive roll 24. Drive roll 24, in turn, is secured to drive shaft 26 that is, in turn, connected to a motor 27 by means of flex coupler 29. Drive shaft 26 also is secured to drive roll 28 which drives belt 30. Belt 30 also is wound about drive roll 36 mounted on drive shaft 34. Drive roll 28 is ratioed to allow for a difference (if any) in the distance traveled by an unloader arm 42 from position 48a to position 48b and the distance the loader arm 16 travels. Drive shaft 34 also is secured to drive roll 32 which supports drive belt 38. Drive belt 38 is wound about idler roll 40 such as a spring loaded idler roll. Drive belt 38 is captured by belt plate 49 and is connected to and moves unloader arm support 46. Unloader arm 42 is connected to the support 46 which rides on slide 48. Slide 48 is positioned so that support 46 moves upwardly and away from support plate 12 when moving in a direction from position 48a toward position 48b. The belt 30 can be replaced with gears, if desired.

A pair of guides 51 and 52 as well as sample stop pins 53 and 54 are provided to properly position a sample plate above slot 14. Stop pin 57 is provided to position a sample plate within an analytical apparatus. For sake of clarity, the analytical apparatus is not shown in FIGS. 1–6. However, the phantom lines shown with respect to apparatus 10 indicate the portion of apparatus 10 included within the analytical apparatus. Pivotally mounted slides 61 and 62 are provided to guide a sample plate above the support 12 and then onto guides 51 and 52 located on support 12. Slides 61 and 62 are pivotally mounted on shaft 63. Although one continuous shaft is depicted, a pair of half shafts may be used if it is desired to keep the area above slot 14 open.

As will be described in more detail below, arm 16 is provided to move a sample plate into the analytical apparatus and unloader arm 42 is provided to remove a sample plate away from the analytical apparatus on an exit path positioned above support 12.

Figure 3:
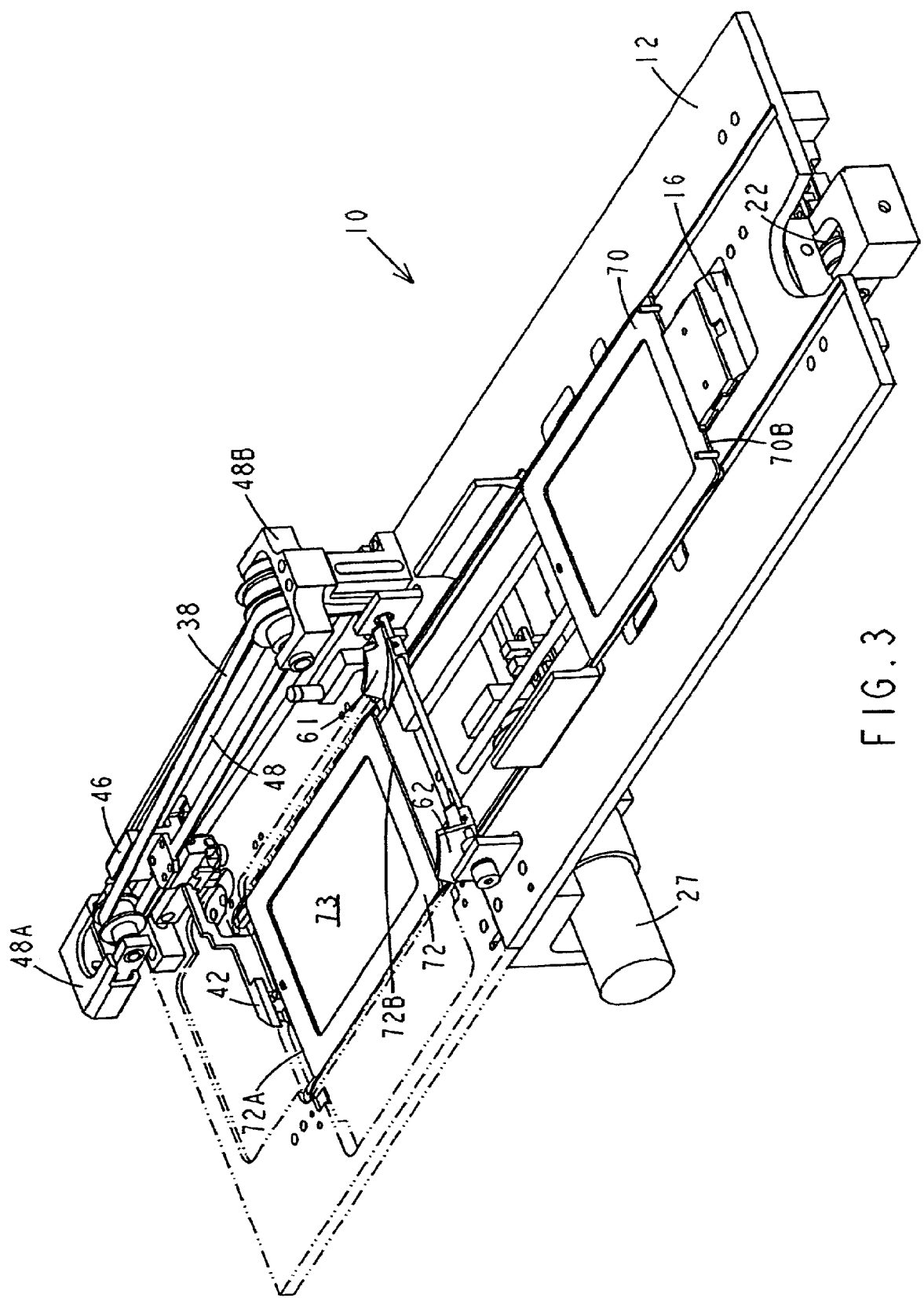
FIG. 3 is a top perspective view of the apparatus of FIG. 1 supporting two sample plates.

Referring to FIG. 3, the transfer apparatus 10 is shown supporting two sample plates 70 and 72, each of which can have a plurality of sample wells. The sample plate 72 is positioned within the analytical apparatus while sample plate 70 is positioned outside the analytical apparatus so that it can be inserted into the analytical apparatus after the samples on plate 72 are analyzed. Loader arm 16 attached to belt 20 is positioned behind plate 70 so that it can push the plate 70 into the position previously occupied by plate 72 as shown.

Unloader arm 42 is mounted on arm support 46 which, in turn, is mounted on slide 48 and attached to belt 38. When the drive shaft is rotated by the motor 27, loader arm 16 pushes sample plate 70 on support 12 toward the plate 72. Simultaneously with movement of plate 70, plate 72 is pushed by unloader arm 42 toward plate 70 and pivotally mounted slides 61 and 62. Slide 48 is angled upwardly away from support 12 so that arm support 46 moves arm 42 upwardly. The leading edge 72b of plate 72 contacts slides 61 and 62 so as to move the plate 72 upwardly over plate 70.

Figure 4:
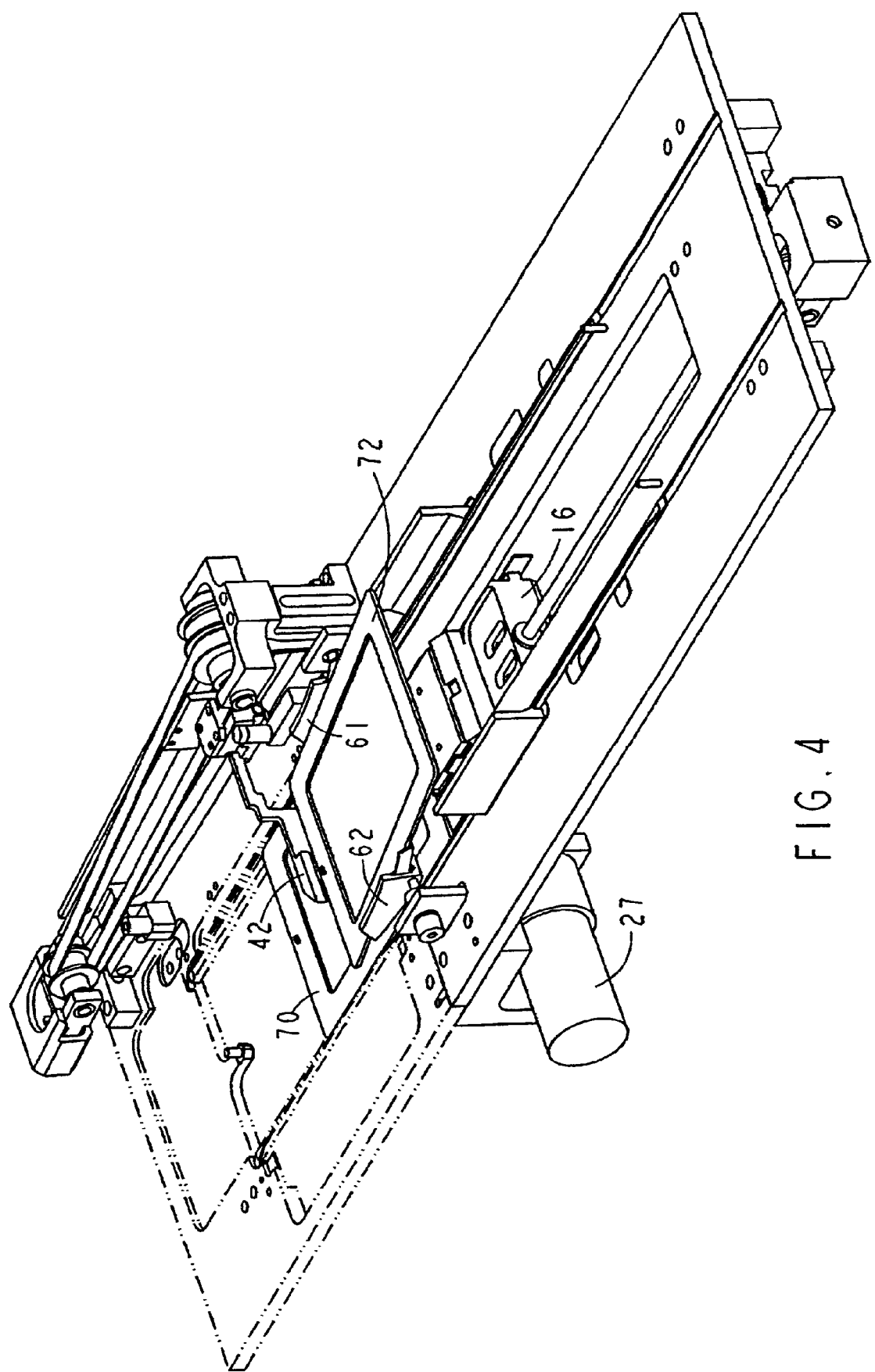
FIG. 4 illustrates, in perspective view, the simultaneous movement of two sample plates with the apparatus of FIG. 1.

As shown in FIG. 4, plate 72 is guided by slides 61 and 62 and moved by unloader arm 42 over plate 70 which, in turn is moved into the analytical apparatus.

Figure 5:
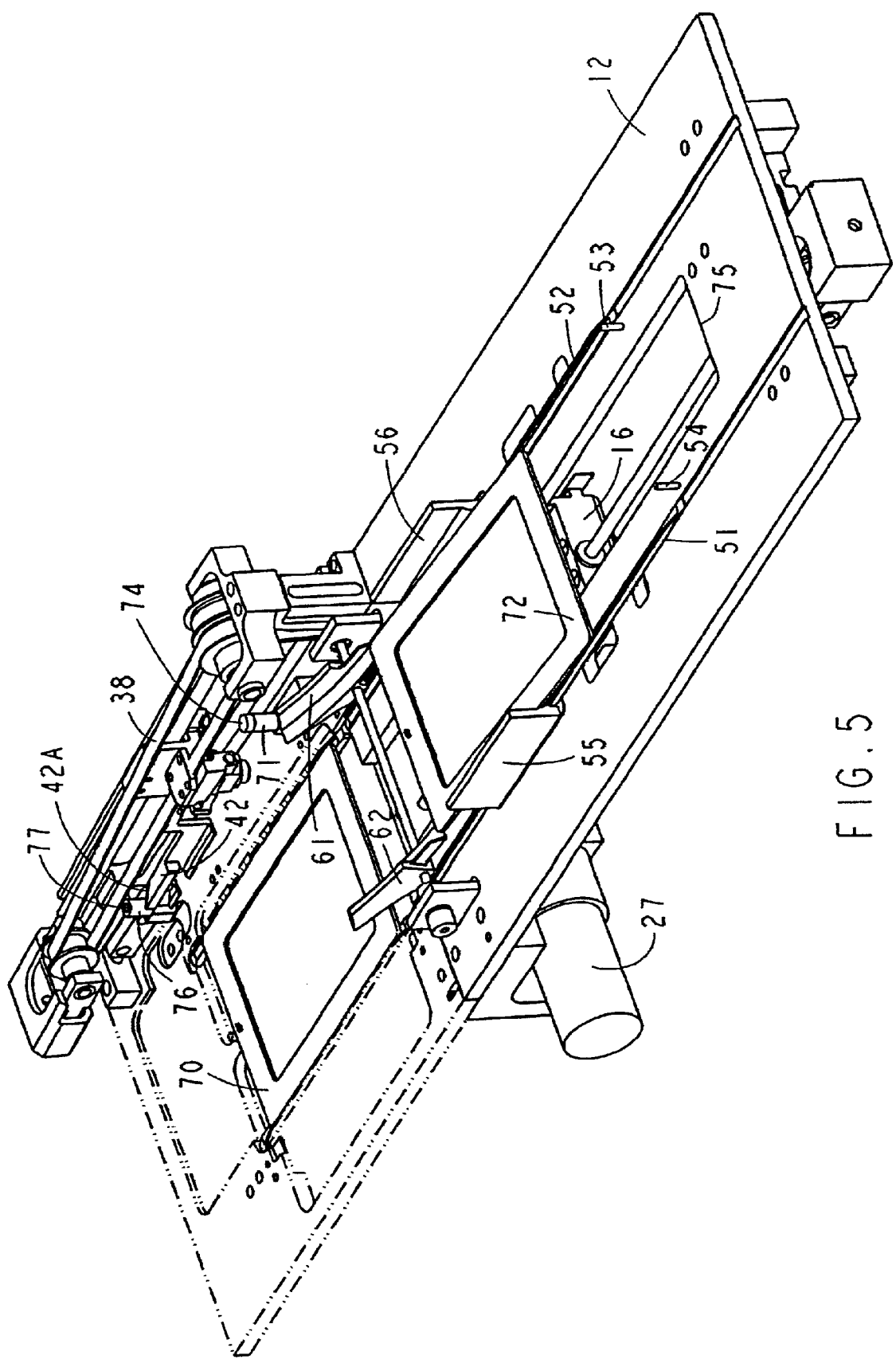
FIG. 5 illustrates, in perspective view, the nearly complete movement of two sample plates with the apparatus of FIG. 1.

As shown in FIG. 5, plate 72 is positioned by side members 55 and 56 onto guides 51 and 52 and above loader arm 16. Arm 16 is moved toward surface 75 under plate 72 so as to be positioned to push a third plate (not shown), which replaces plate 72, to be analyzed in the analytical apparatus with a plate movement cycle the same as described above.

Figure 6:
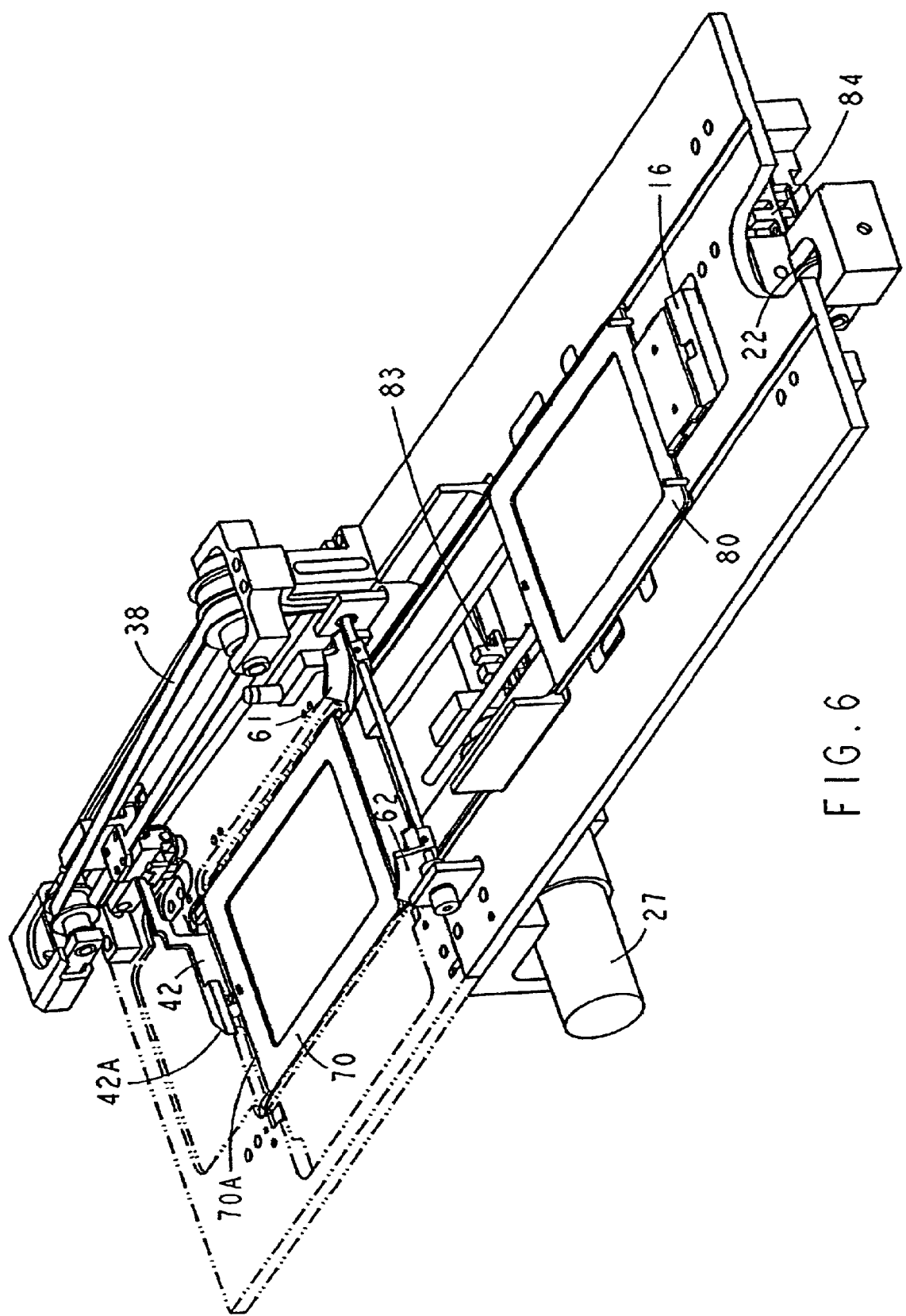
FIG. 6 illustrates, in perspective view, a replacement of a first sample plate with a third sample plate with the apparatus of FIG. 1.

As shown in FIG. 6, a third plate 80 is positioned to be pushed by loader arm 16 into the analytical apparatus in the same manner as described above for the movement of plate 70 into the analytical apparatus. Similarly, plate 70 is moved in the same manner as described above for plate 72 out of the analytical apparatus. Arm 42 can be positioned away from the trailing edge 70a of plate 70 to allow for vertical movement of plate 70 within the analytical apparatus.

The general operation of the apparatus of this invention will be described with reference to FIGS. 3–6 wherein FIG. 3 represents the position of the apparatus at the beginning of a sample plate transfer cycle. As shown in FIG. 3, unloader arm 42 is positioned proximate the trailing edge 72a of sample plate 72 while loader arm 16 is positioned in contact with the leading edge 70b of sample plate 70. Sample plate 72 is positioned within the analytical apparatus, for example, at a reading station, while sample plate 70 is positioned outside the analytical apparatus, for example, at a loading station.

When analysis of the samples in sample wells 73 of sample plate 72 is complete, the motor 27, which can be a stepping motor, DC motor, servo motor or the like, is activated to rotate shaft 26 which causes belts 30, 38 and 20 to rotate clockwise. The rotation of belts 30 and 38 effects movement of unloader arm 42 to effect movement of plate 72 toward pivotally mounted slides 61 and 62. Upon contact of plate 72 with contact slides 61 and 62, plate 72 is caused to move onto slides 61 and 62 and over plate 70 in a manner to prevent collision of plates 70 and 72 (FIG. 4). Simultaneously with this movement of plate 72, loader arm 16 pushes plate 70 under plate 72 to position it in the analytical apparatus for placement at the reading station (See FIG. 5). A pair of sensors 83 and 84, each of which can be an optical detector, contact switch, or the like, senses the position of loader arm 16 and stops its motion at the end of desired travel to properly position the plates 70 and 72. At a predetermined time, the sensor actuates reversal of the motor 27 to reverse the direction of rotation of shaft 26 to reposition the unloader arm 42 and the loader arm 16 in the position shown in FIG. 3. Sample plate 72, now located at the loading station, then is replaced either manually or by a robot by sample plate 80 (FIG. 6) and the sample plate transport cycle is repeated. The spring loaded arm 42 is moved to the position shown in FIG. 5 by contact of the arm driven by belt 38 with rotatable collar 71 positioned on capped post 74. The unloader arm 42 is moved from the position shown in FIG. 5 to the position shown in FIG. 6 by the contact of the beveled surface 42a of the arm 42 with the rotatable collar 76 positioned on post 77 which causes the spring loaded arm 42 to snap into the position shown in FIG. 6. Rotatable collars are used to minimize wear.

Figure 7A:
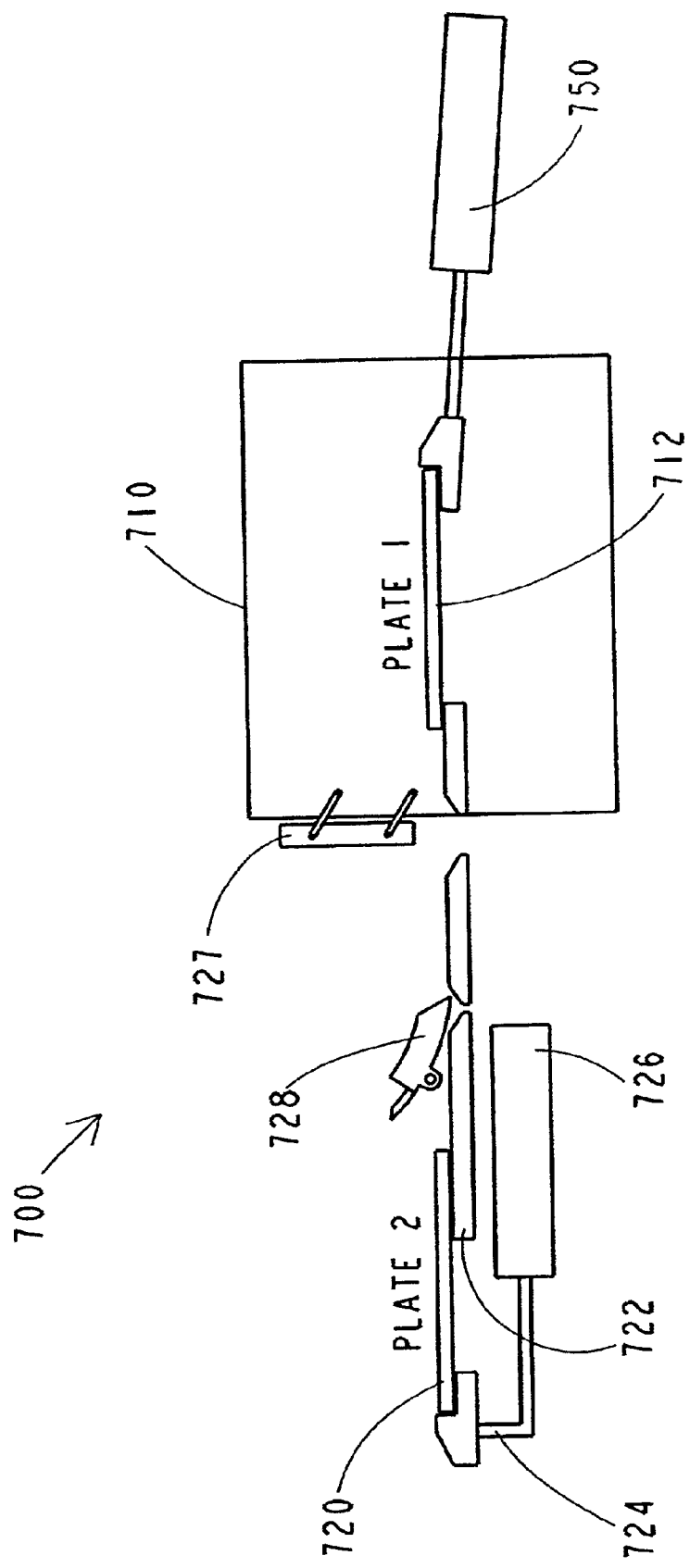
FIG. 7A is a schematic representation, in side view, of a vacuum sample holding/analysis chamber of a MALDI mass spectrometer showing the transfer of sample plates through use of the apparatus of the present invention.

In one preferred embodiment, the transfer apparatus 10 of the present invention is used in conjunction with a MALDI time-of-flight (TOF) mass spectrometer system to enhance the throughput of the system. A representative mass spectrometer system is described in U.S. Pat. No. 5,498,545 whose disclosure is incorporated by reference herein. FIG. 7A shows a transfer apparatus 700, that is similar in design and operation in all material aspects to the apparatus described with respect to FIGS. 1–6, coupled to a sample holding chamber 710 of a MALDI-TOF mass spectrometer. The holding chamber is maintained under moderate vacuum conditions and is shown with sample plate 712 in position to be transferred to an analysis chamber 714 (see FIG. 7B) or alternatively to be removed from the mass spectrometer. The analysis chamber is kept at a lower vacuum by pumps and valves (not shown) in customary fashion as further described in the aforementioned U.S. Pat. No. 5,498,545. Gripper 718 (see FIG. 7B) is used to grab the sample plate 712 and place it in position for laser desorption and subsequent ionization of samples in the analysis chamber 714. A second sample plate 720 resting on holders 722 and 723 is positioned outside the mass spectrometer. A loader arm 724 driven by pneumatic actuator 726 operates to move sample plate 720 toward plate 712 and plate 712 is driven by actuator 750 at the time a plate exchange is desired. The sample holding chamber 710, which functions as a load lock, is vented to atmosphere and flap door 727 is opened to permit the exchange of plates 712 and 720. A pair of pivotally mounted slides 728 and 729 are used, as described with respect to the embodiments depicted in FIGS. 1–6, to allow the plate 712 to proceed along an exit path positioned above the entry path for sample plate 720 to permit the simultaneous exchange of sample plates.

FIG. 7B shows the various positions that MALDI sample plates occupy during an analysis cycle. Region 1, within the analysis chamber 714, is the analysis position where the sample plate is positioned for irradiation by a laser (not shown). Region 2, within the sample holding chamber 710, is an intermediate or transfer position where a second sample plate either awaits introduction into the analysis chamber 714 or removal from the instrument system. Region 3, outside the instrument, represents an exchange position where a third sample plate awaits introduction into the mass spectrometer. Regions 2 and 3 involve simultaneous plate exchange by use of the transfer apparatus 700 as described above. Actuator 752 moves a sample plate between regions 1 and 2 in accordance with the teachings of U.S. Pat. No. 5,498,545. The exchange of plates at region 3 may be effectuated either manually or through use of a robotic system.

Figure 8:
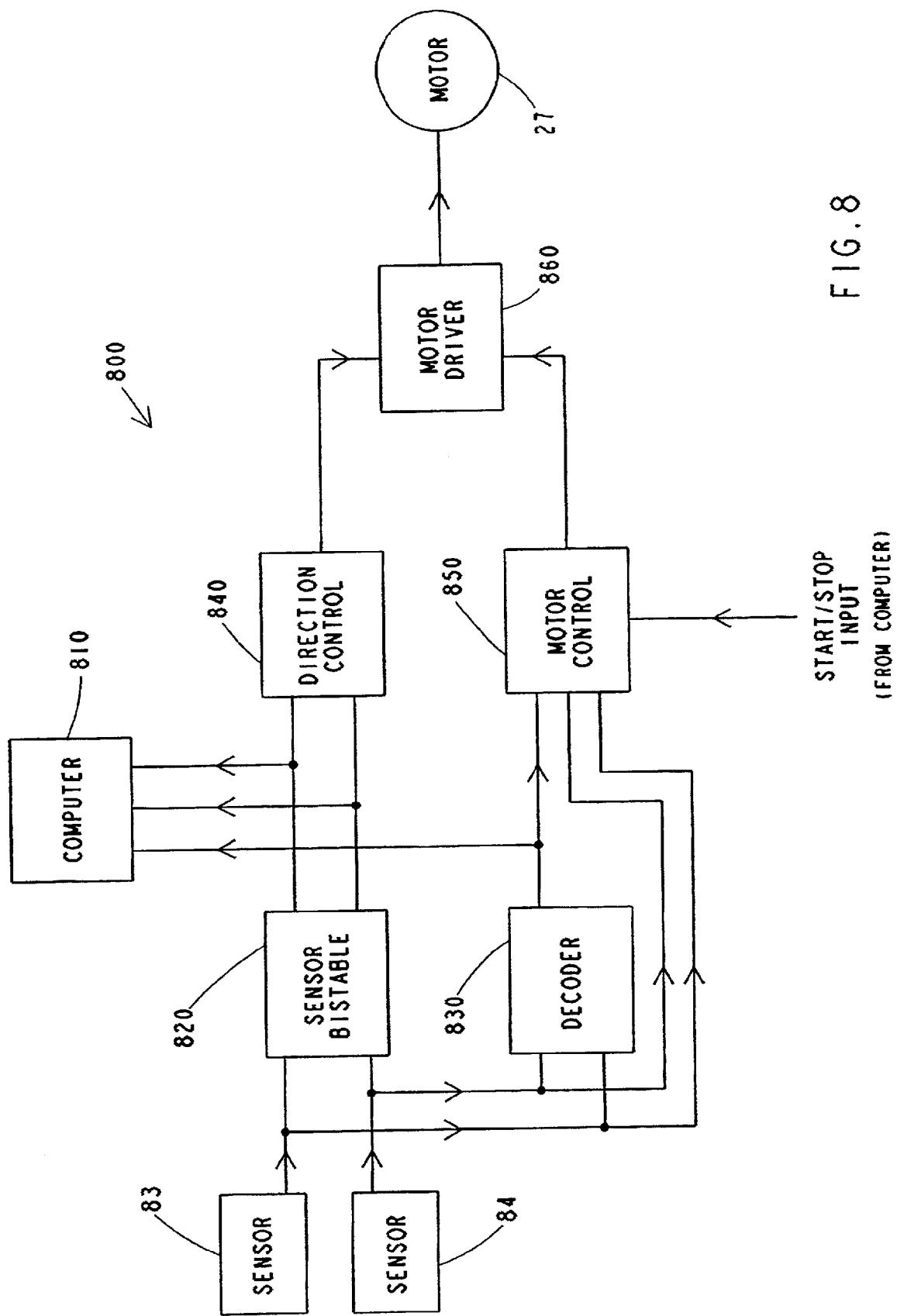
FIG. 8 is a block diagram illustrating the operation of the electrical circuit for controlling belt movement in the apparatus of FIG. 1.

FIG. 8 shows a block diagram of the control circuit that effects the desired plate movement of the transfer apparatus of the present invention. The control circuit 800 that controls the plate exchange transfer apparatus 10 has the capability to control the complete plate cycle with no intervention, aside from start/stop inputs from computer 810 and automatically reverses the motor direction when a new plate is loaded.

The control circuit 800 receives inputs from the sensors 83 and 84. These sensors detect when a plate has reached the desired position at both ends of the transfer apparatus, one sensor positioned at the loading station, and the other at the reading station. A sensor bistable circuit element 820 "remembers" the state of the sensors while the plates are travelling. This element only changes state once a plate activates a sensor, indicating that the plate has reached the desired position. A decoder circuit element 830 compares the sensor states and generates a signal which informs computer 810 of whether the position of the plates are in between sensors, or at the ends of their travel. A direction control circuit element 840 determines the direction the motor should move, based on the last known position of the plates, as stored in the sensor bistable circuit 820. A motor control circuit element 850 applies power to the motor 27 in order to make the transfer apparatus run. As explained in more detail below, the direction of rotation and duration of the movement are determined by the direction control 840 and motor control 850 circuit elements, respectively.

The following describes how all of the circuit elements of the control circuit 800 work together to correctly execute one complete plate exchange cycle. For the purposes of this description, a "forward" motion of the motor 27 will refer to the movement of a new plate from the loading station toward the reading station. Also, the sensors 83 and 84 used in this embodiment are optical sensors which are activated/de-activated by flags (not referenced in FIGS. 1–6).

1. At the end of the previous cycle, the arrival of a plate from the reading station to the loading station sets the sensor bistable element 820 into the "forward" position, and stops the motor 27.
2. The robot arm (or some other means) removes the "read" plate and places a new plate in the loading station. Since the flags that activate the sensors 83 and 84 are attached to the transfer apparatus 10, and not to the plates, removal and replacement of a plate does not affect the state of the sensor bistable element 820.
3. Once a new plate has been loaded, the computer 810 sends a pulse to the motor control circuit element 850 via the start/stop input. The motor control circuit applies power to the motor 27 through the motor driver 860, and the direction control circuit element 840 ensures the polarity is such that the motor moves in the forward direction.
4. As the new plate leaves the loading station, the sensor 84 is de-activated. The sensor bistable element 820 does not change state on de-activation of either sensor, thus the direction is still set to forward. With both sensors deactivated, the decoder circuit element 830 output registers that the plate is between limits of the respective sensors. The motor control circuit element 850 uses this signal to determine the effect of the next pulse from the start/stop input. While both sensors are deactivated, a pulse from the computer 810 will stop the motor 27. If either sensor is active, a pulse from the computer will start the motor. In this way, the computer does not need to determine the state of the transfer apparatus before sending a pulse, and the pulse can always be of the same type. The motor control circuit element 850 will automatically choose the correct response when the pulse arrives.
5. While the new plate travels towards the reading station, the old plate leaves the reading station and moves towards the loading station. The design and construction of the transfer apparatus 10 ensures that the two plates pass each other and that the new plate reaches its destination first.
6. When the new plate reaches the reading station, the sensor 83 is activated, and this sets the sensor bistable circuit element 820 into the "reverse" direction. The output of this element causes the direction control circuit element 840 to reverse the polarity of the power applied to the motor 27. The decoder circuit element 830 also registers that a plate has arrived at its destination, and its output is passed to the motor control circuit element 850. In this mode the motor control circuit element 850 leaves power applied to the motor. The motor 27 therefore reverses direction and the transfer apparatus 10 begins to run "backwards".
7. When the transfer apparatus 10 reverses direction, the new plate remains behind in the reading station, and the old plate has not yet reached the loading station. Sensor 83 remains de-activated but, as before, this has no effect on the sensor bistable circuit element 820, which maintains the backwards status of the transfer apparatus. The output of the decoder circuit element 830 now registers that the plate is between limits of the sensors 83 and 84. The returning transfer apparatus "picks up" the old plate and conveys it back toward the loading station.

8. When the old plate reaches the loading station, sensor 84 is activated, and this sets the sensor bistable circuit element 820 into the "forward" direction. The output of this element causes the direction control circuit element 840 to reverse the polarity of the power applied to the motor 27. The decoder circuit element 830 also registers that a plate has arrived at its destination, and its output is passed to the motor control circuit element 850. In this mode the motor control circuit cuts power to the motor. The motor thus stops and the plate exchange has been completed. The system is left in the same state as step #1, ready for the old plate to be removed.

Since, as previously mentioned, the sensor-activating flags are attached to the transfer apparatus and not to the plates, the cycle will execute correctly at the very beginning of a run (when there is no old plate in the reading station) and at the end of a run (when the last old plate is ejected).

Referring to FIGS. 9A, 9B, 10A and 10B, an alternative apparatus of this invention is shown. The arm 90 replaces arm 42 to push sample plate 72 parallel to support plate 12 onto slides 61 and 62. The arm 90 is pivotable about rod 92 which extends the length of arm 90. The arm 90 includes flanges 94 and 96. When the arm 90 contacts plate 72, it is pivoted about rod 92 so that flange 96 lifts plate 72 while flange 94 contacts the trailing edge 95 to push it out of the analytical apparatus while preventing the plate from prematurely pivoting during movement.

It is to be understood that the arms for moving the sample plates by pulling the sample plates into position can be replaced by placing grippers on the driven belts which grip the appropriate edge of the sample plates.

What is claimed is:

1. The process for positioning a first sample plate in an analytical apparatus and for removing a second sample plate from the analytical apparatus which comprising:
   (a) moving said first sample plate into said analytical apparatus along an entry path having a first direction; and
   (b) concomitantly with step (a) moving said second sample plate from said analytical apparatus along an exit path in a second direction opposite said first direction, at least a portion of which is vertically spaced apart from said entry path and which prevents collision of said first sample plate with said second sample plate.

2. Apparatus for positioning a first sample plate in an analytical apparatus and for removing a second sample plate from the analytical apparatus which comprises:
   (a) means for moving said first sample plate into said analytical apparatus along an entry path having a first direction; and
   (b) means for moving said second sample plate concomitantly with movement of said first sample plate from said analytical apparatus along an exit path in a second direction opposite said first direction, at least a portion of which is positioned in a vertically spaced apart position from said entry path while avoiding collision of said first sample plate with said second sample plate.

3. The process of claim 1 wherein a portion of said entry path is positioned below said exit path.

4. The process of claim 1 wherein a portion of said entry path is positioned above said exit path.

5. The apparatus of claim 2 wherein a portion of said entry path is positioned below said exit path.

6. The apparatus of claim 2 wherein a portion of said entry path is positioned above said exit path.

7. The apparatus of claim 2 including means for reversing said a first direction for moving said first sample plate and said second direction for moving said second sample plate after completing moving said first sample plate by means (a) and said second plate by means (b).

8. The apparatus of claim 5 including means for reversing said first direction for moving said first sample plate and said second direction for moving said second sample plate after completing moving said first sample plate by means (a) and said second plate by means (b).

9. The apparatus of claim 6 including means for reversing said first direction for moving said first sample plate and said second direction for moving said second sample plate after completing moving said first sample plate by means (a) and said second plate by means (b).

10. The process of claim 1 wherein said first direction for moving said first sample plate and said second direction for moving said second sample plate are reversed after completing moving said first sample plate by step (a) and said second plate by step (b).

11. The process of claim 3 wherein said first direction for moving said first sample plate and said second direction for moving said second sample plate are reversed after completing moving said first sample plate by step (a) and said second plate by step (b).

12. The process of claim 4 wherein said first direction for moving said first sample plate and said second direction for moving said second sample plate are reversed after completing moving said first sample plate by step (a) and said second plate by step (b).

13. The apparatus of claim 2 wherein the analytical apparatus comprises a MALDI-TOF mass spectrometer.

14. The process of claim 1 wherein the analytical apparatus comprises a MALDI-TOF mass spectrometer.

15. The apparatus of claim 6 wherein the analytical apparatus comprises a MALDI-TOF mass spectrometer.

16. The apparatus of claim 7 wherein the analytical apparatus comprises a MALDI-TOF mass spectrometer.

17. A sample plate transport device for an analytical apparatus comprising:
   a first movable transport member for holding a first sample plate and for moving the first sample plate toward or away from the analytical apparatus along a first path having a first direction;
   a second movable transport member for holding a second sample plate and for moving the second sample along a second path different from the first path and in a second direction opposite the first direction;
   wherein the first and second sample plates are moved concomitantly toward or away from the analytical apparatus and at least a portion of the first and second paths are positioned in a vertically spaced apart position to avoid collision of the first sample plate with the second sample plate during movement thereof.

18. The device of claim 17 wherein a portion of the first path is positioned below the second path.

19. The device of claim 17 wherein a portion of the first path is positioned above the second path.

20. The device of claim 17 wherein the analytical apparatus comprises a MALDI-TOF mass spectrometer.

* * * * *